US00PP27635P3

(12) United States Plant Patent
Yamada

(10) Patent No.: US PP27,635 P3
(45) Date of Patent: Jan. 31, 2017

(54) ***PETUNIA* PLANT NAMED 'SUNPETU 3881'**

(50) Latin Name: *Petunia×hybrida*
Varietal Denomination: Sunpetu 3881

(71) Applicant: SUNTORY FLOWERS LIMITED, Tokyo (JP)

(72) Inventor: Masahiro Yamada, Kanagawa (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 77 days.

(21) Appl. No.: 14/121,575

(22) Filed: Sep. 19, 2014

(65) Prior Publication Data

US 2015/0089704 P1 Mar. 26, 2015

Related U.S. Application Data

(60) Provisional application No. 61/960,553, filed on Sep. 20, 2013.

(51) Int. Cl.
*A01H 5/02* (2006.01)

(52) U.S. Cl.
USPC ..... Plt./356.21
CPC ..... *A01H 5/02* (2013.01)

(58) Field of Classification Search
USPC ..... Plt./356.21
See application file for complete search history.

(56) References Cited

U.S. PATENT DOCUMENTS

PP18,229 P2 * 11/2007 Ishihara et al. ..... Plt./356.21
PP24,350 P2 * 3/2014 Isobe ..... Plt./356.21
PP25,384 P2 * 3/2015 Kanaya et al. ..... Plt./413
PP26,270 P2 * 12/2015 Kanaya et al. ..... Plt./413
2014/0215669 P1 7/2014 Tsukahara

OTHER PUBLICATIONS

Lamont Calibrachoa—have you tried them yet? May 21, 2012, retrieved on Feb. 24, 2016, retrieved from the Internet at <http://davesgarden.com/guides/articles/view/3712#b> 2 pp.*
Midwest Gardening There might be just a little more to selecting the right *Petunia* than you thought, retrieved on Feb. 24, 2016, retrieved from the Internet at <http://www.midwestgardentips.com/selecting_petunias.html> 5 pp.*
"2012 Spring-Summer gardening catalog," Daiichi Engei Co., Ltd., Oct. 2011, pp. 8-9.
Registration No. 22221, Registration date Jan. 28, 2013, Suntory Flowers Company, 1 page.

* cited by examiner

*Primary Examiner* — June Hwu
(74) *Attorney, Agent, or Firm* — Kilpatrick Townsend & Stockton LLP

(57) ABSTRACT

Disclosed herein is a new and distinct variety of *Petunia* plant having vigorous and semi-trailing habit, abundant flowering, the whole bush remaining in bloom for a considerable period of time, and single, small sized and vivid red purple colored flowers.

2 Drawing Sheets

Botanical designation: *Petunia×hybrida.*
Cultivar denomination: 'Sunpetu 3881'.

BACKGROUND OF THE INVENTION

The present invention relates to a new and distinct variety of *Petunia* plant, which is hereinafter referred to as 'Sunpetu 3881'.

A *Petunia* is a very popular plant that is used in flower bedding and potting in the summer season.

This purpose of this invention is to obtain a new *Petunia* cultivar with vigorous and semi-trailing habit, abundant flowering, the whole bush remaining in bloom for a considerable period of time, and single, small sized and vivid red purple colored flowers.

The new *Petunia* plant originated from cross-pollination of the female parent 'Shiro2' and the male parent 'MS22-193-2'. The female parent 'Shiro2' (unpatented) used in the crossing of 'Sunpetu 3881' is a strain of the applicant's breeding lines (i.e., proprietary *Petunia* selection), having white petals, and the male parent 'MS22-193-2' (unpatented) used in the crossing of 'Sunpetu 3881' is a strain of the applicant's breeding lines (i.e., proprietary *Petunia* selection), having medium flower diameter. The cross-pollination was conducted in Sep. 10, 2010 at Yame-gun, Fukuoka, Japan.

In March 2011, the seedlings obtained by the crossing were planted in a field. In May 2011, some seedlings were selected in view of growth habit, flower size and color thereof. Shortly thereafter stem tip culturing was carried out, and then the propagation was started.

In November 2012, the cultivation of the seedlings was repeated. The botanical characteristics of that plant were then examined, using similar varieties 'Daiichi Bluette Purple 2' and 'MP22-21-2' (unpatented) for comparison. As a result, it was concluded that this *Petunia* plant is distinguishable from any other variety, whose existence is known, and is uniform and stable in its characteristics.

The new variety of Petunia plant was then named 'Sunpetu 3881'.

SUMMARY OF THE INVENTION

This new variety is unlike any *Petunia* commercially available as evidenced by the following unique combinations of characteristics.

1. Vigorous and semi-trailing habit.
2. Abundant flowering, the whole bush remaining in bloom for a considerable period of time.
3. Single, small sized and vivid red purple colored flower.

The new variety 'Sunpetu 3881' differs from the similar variety 'Daiichi Bluette Purple 2', which is disclosed in U.S. Plant Pat. No. 22,236, in the following points.

1. The plant posture of 'Sunpetu 3881' is considerable trailing. That of 'Daiichi Bluette Purple 2' is trailing.
2. The stem length of 'Sunpetu 3881' is long. That of 'Daiichi Bluette Purple 2' is medium.

The new variety 'Sunpetu 3881' differs from the similar variety 'MP22-21-2' in the following points.

1. The flower diameter of 'Sunpetu 3881' is medium. That of 'MP22-21-2' is somewhat small.
2. The number of colors on surface of corolla lobe of 'Sunpetu 3881' is one. That of 'MP22-21-2' is two.

This new variety of *Petunia* plant 'Sunpetu 3881' was asexually reproduced by the use of cuttings in Higashiomi, Shiga, Japan, and homogeneity and stability thereof were confirmed. A cutting used to reproduce the new variety typically has one or more leaves and a stem. The instant plant retains its distinctive characteristics and produces true to type in successive generations.

BRIEF DESCRIPTION OF THE PHOTOGRAPHS

The depicted plants had been reproduced by the use of cuttings and were photographed during October 2013 while growing outdoors in wall pots with about 24 cm of container size at an age of approximately 5 months.

FIG. 1 is a photograph of a typical plant of the new variety of *Petunia* plant 'Sunpetu 3881' while growing in a pot.

FIG. 2 is a photograph of a close view of flowers of the new variety of *Petunia* plant 'Sunpetu 3881'.

DETAILED BOTANICAL DESCRIPTION

In October 2013, the cultivation of the seedlings was repeated at Higashiomi, Shiga, Japan. The average day temperature was about 23° C., and the average night temperature was about 13° C. The plants were grown under natural sunlight. The number of days to flowering (response time) was 2-3 weeks. The quality was maintained for about 150 days. The plants had temperature resistance to about −5° C. (the lowest temperature) and about 35° C. (the highest temperature). Further, the plants had good tolerance to pests and pathogens.

For the parentage information: The female parent 'Shiro2' (unpatented) used in the crossing of 'Sunpetu 3881' is a strain of the applicant's breeding lines (i.e., proprietary selection of *Petunia×hybrida*), having white petals, and the male parent 'MS22-193-2' (unpatented) used in the crossing of 'Sunpetu 3881' is a strain of the applicant's breeding lines (i.e., proprietary selection of *Petunia×hybrida*), having medium flower diameter.

For the propagation information: approximate soil and/or air temperature was around 15-20° C.; the new cultivar was propagated by cutting; number of days to initiate roots was about 7 days; number of days to produce a rooted young plant was about 21 days; free-root branching; root color was white; and root texture was fibrous.

The botanical characteristics of the new and distinct variety of *Petunia* plant named 'Sunpetu 3881' at an age of approximately 5 months are shown in the following TABLE 1. In the following description, the color-coding is in accordance with The Horticultural Colour Chart of The Royal Horticultural Society, London, England (R.H.S. Colour Chart The 5th edition 2007).

TABLE 1

PLANT VARIETY DESCRIPTION

| CHARACTERISTIC | APPLICATION VARIETY Sunpetu 3881 |
|---|---|
| ANNUAL, BIENNIAL or PERENNIAL? | Grown as annual |
| TYPE OF PLANT: i.e., TREE, SHRUB, SUBSHRUB, VINE, CUT FLOWER, POTTED PLANT | Potted plant |
| APPROPRIATE CONTAINERS +/or CROPPING SYSTEM | Ideal for pots, hanging baskets or planters, and is good for use as a ground cover. |
| GROWTH HABIT | Semi-trailing |
| PLANT HEIGHT | About 28.0 cm |
| PLANT DIAMETER OR AREA OF SPREAD | About 65.0 cm |
| PLANT VIGOR | Vigorous |
| BRANCHING HABIT | Freely branching |
| BASAL BRANCHING? | Present |
| PINCHING REQUIRED? | Required |
| NUMBER OF LATERAL BRANCHES | Many |
| LATERAL BRANCH LENGTH | About 25.5 mm |
| LATERAL BRANCH DIAMETER | About 2.1 mm |
| INTERNODE LENGTH OF A STEM | About 29.6 mm |
| STEM ASPECT | Upright to outward |
| STEM COLOR (and bark color, if applicable) | Near 143A RHS |
| STEM PUBESCENCE? | Pubescent |
| OTHER PLANT/STEM CHARACTERISTICS | |
| LEAF ARRANGEMENT | Alternate |
| COMPOUND OR SIMPLE? | Simple |
| QUANTITY OF LEAVES PER LATERAL BRANCH | Many |
| LEAF SHAPE | Ovate |
| LEAF TIP | Acute |
| LEAF BASE | Obtuse |
| LEAF LENGTH | About 36.4 mm |
| LEAF WIDTH | About 18.7 mm |
| LEAF THICKNESS | About 0.2 mm |
| LEAF TEXTURE | Smooth |
| LEAF PUBESCENCE? WHICH SIDE? | Pubescent, both sides |
| LEAF MARGIN | Entire |
| VENATION PATTERN | Pinnate |
| LEAF COLOR, YOUNG, UPPER SIDE | Near 138A RHS |
| LEAF COLOR, YOUNG, UNDER SIDE | Near 138B RHS |
| LEAF COLOR, MATURE, UPPER SIDE | Near 138A RHS |
| LEAF COLOR, MATURE, UNDER SIDE | Near 138B RHS |
| VENATION COLOR, UPPER SIDE | Near 144C RHS |
| VENATION COLOR, UNDER SIDE | Near 144D RHS |
| PETIOLE LENGTH | About 5.3 mm |
| PETIOLE DIAMETER | About 1.8 mm |
| PETIOLE TEXTURE | Pubescent, dense, long |
| PETIOLE COLOR | Near 144C RHS |
| STIPULES, TENDRILS, THORNS, SPINES OR PRICKLES? IF SO, GIVE COLOR AND SIZE | |
| OTHER FOLIAGE CHARACTERISTICS | |
| FLOWER ARRANGEMENT | Borne in upper leaf axils |
| INFLORESCENCE TYPE OR FORM (if applicable) | Flower solitary |
| FLOWER TYPE or FORM | Single |
| FLOWERING HABIT | Continuously |
| QUANTITY OF FLOWERS PER LATERAL STEM | About 1 to 4 |
| QUANTITY OF FLOWERS PER PLANT | About 183 |
| NATURAL FLOWERING SEASON | About Spring to late Autumn |
| TIME TO FLOWER OR RESPONSE TIME | About 2~3 weeks |
| FRAGRANCE | Absent |
| FLOWER BUD LENGTH | About 20.7 mm |
| FLOWER BUD DIAMETER | About 5.4 mm |

TABLE 1-continued

| PLANT VARIETY DESCRIPTION | |
|---|---|
| CHARACTERISTIC | APPLICATION VARIETY Sunpetu 3881 |
| FLOWER BUD SHAPE | Cylindrical with 5 lines, Tip: twisted |
| FLOWER BUD COLOR | Near 79C RHS |
| FLOWER ASPECT; i.e., UPRIGHT, OUTWARD, DROOPING, etc. | Upright to outward |
| FLOWER SHAPE | Salverform |
| FLOWER DIAMETER | About 26.9 mm |
| FLOWER DEPTH (HEIGHT) | About 24.0 mm |
| FLOWER LONGEVITY ON PLANT | About 7~10 days |
| PERSISTENT OR SELF-CLEANING? | Self-cleaning |
| PETAL TEXTURE, UPPER SURFACE | Smooth |
| PETAL TEXTURE, LOWER SURFACE | Smooth |
| TUBE TEXTURE, | Pubescent |
| PETAL ARRANGEMENT | Single whorl |
| PETAL NUMBER | 5 |
| PETALS FUSED? | Fused |
| PETAL SHAPE | Spatulate |
| PETAL MARGIN | Entire |
| PETAL TIP | Mucronate |
| PETAL BASE | Fused |
| PETAL LENGTH | About 11.9 mm |
| PETAL WIDTH | About 12.3 mm |
| PETAL COLOR, WHEN OPENING, UPPER SIDE | Near 72A RHS |
| PETAL COLOR, WHEN OPENING, LOWER SIDE | Near N80C RHS |
| PETAL COLOR, FULLY OPENED, UPPER SIDE | Near N74A RHS |
| PETAL COLOR, FULLY OPENED, LOWER SIDE | Near 84C RHS |
| PETAL COLOR, FADING TO | — RHS |
| THROAT DIAMETER | About 8.8 mm |
| TUBE DIAMETER (PROXIMAL END) | About 3.1 mm |
| TUBE LENGTH | About 16.3 mm |
| THROAT COLOR (inside) | Near 83D and N92A |
| TUBE COLOR (outside) | Near 83C RHS |
| SEPAL ARRANGEMENT | Single whorl |
| NUMBER OF SEPALS | 5 |
| SEPAL SHAPE | Narrow elliptic |
| SEPAL MARGIN | Entire |
| SEPAL TIP | Obtuse |
| SEPAL BASE | Fused |
| SEPAL LENGTH | About 12.0 mm |
| SEPAL WIDTH | About 2.3 mm |
| SEPAL COLOR, IMMATURE, UPPER SIDE | Near 143B RHS |
| SEPAL COLOR, IMMATURE, UNDER SIDE | Near 143C RHS |
| SEPAL COLOR, MATURE, UPPER SIDE | Near 143B RHS |

TABLE 1-continued

| PLANT VARIETY DESCRIPTION | |
|---|---|
| CHARACTERISTIC | APPLICATION VARIETY Sunpetu 3881 |
| SEPAL COLOR, MATURE, UNDER SIDE | Near 143C RHS |
| CALYX SHAPE | Tubular, star shape |
| CALYX LENGTH | About 9.0 mm |
| CALYX DIAMETER | About 13.7 mm |
| PEDUNCLE LENGTH | About 15.1 mm |
| PEDUNCLE DIAMETER | About 0.7 mm |
| PEDUNCLE ANGLE | Upright to outward |
| PEDUNCLE TEXTURE | Pubescent |
| PEDUNCLE COLOR | Near 144A, Near the calyx: with 77A RHS Anthocyanin 5 |
| STAMEN NUMBER | 5 |
| STAMEN LENGTH | About 10.6~13.5 mm |
| ANTHER SHAPE | Ellipsoidal |
| ANTHER SIZE | About 2.1 × 1.5 mm |
| ANTHER COLOR | Near 93C RHS |
| AMOUNT OF POLLEN | Moderate |
| POLLEN COLOR | Near 93D RHS |
| PISTIL NUMBER | 1 |
| PISTIL LENGTH | About 11.4 mm |
| STIGMA SHAPE | Transversely ellipsoidal |
| STIGMA COLOR | Near 92B RHS |
| STYLE COLOR | Near 145D RHS |
| OVARY COLOR | Near 146D RHS |
| OTHER FLOWER CHARACTERISTICS | |
| QUANTITY OF SEEDS | Seed production has not been observed. |
| Fruit | This variety will bear fruit but no fruits are produced up to date |
| ROOT STRUCTURES such as BULBS, CORMS or RHIZOMES? | Fibrous root |
| LOW TEMPERATURE TOLERANCE | Good |
| HIGH TEMPERATURE TOLERANCE | Good |
| DISEASE RESISTANCE AND/OR SUSCEPTIBILITY | — |
| RESISTANCE OF PESTS AND/OR SUSCEPTIBILITY | — |

This new variety of *Petunia* plant having the above botanical characteristics is suitable for flower bedding and potting, particularly in hanging pots or planters.

It is claimed:

1. A new and distinct variety of *Petunia* plant named 'Sunpetu 3881', substantially as herein illustrated and described.

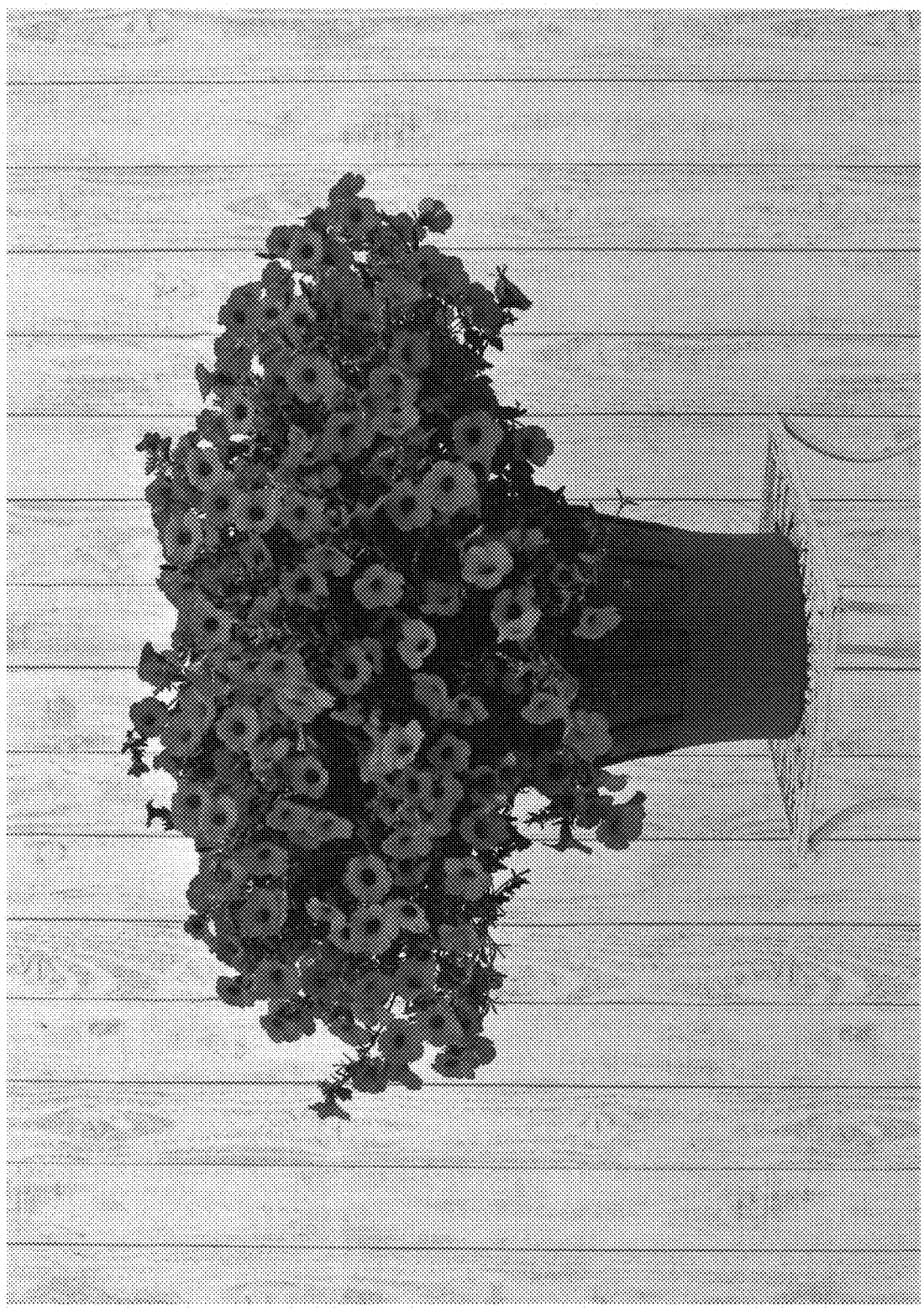

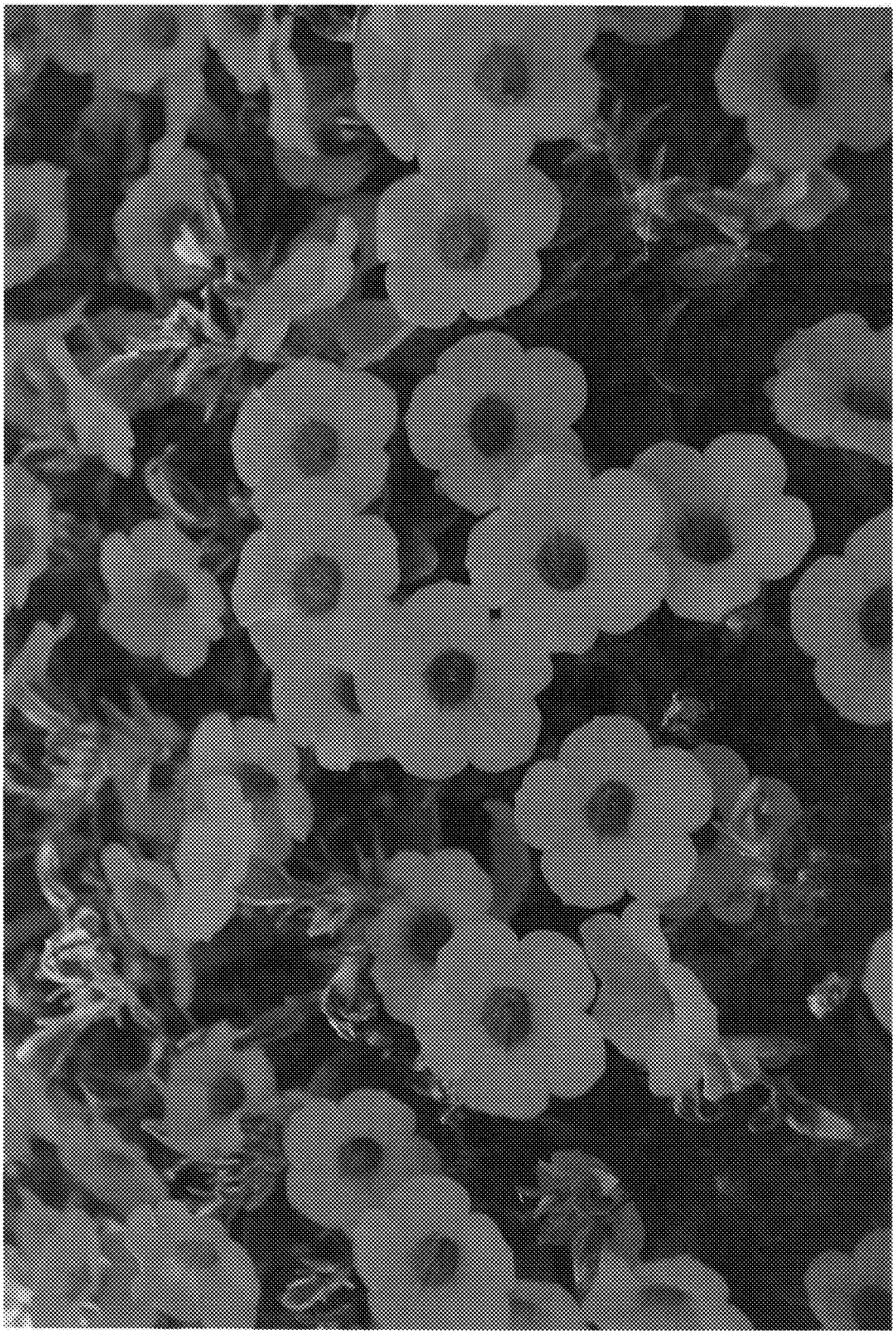

* * * * *